United States Patent [19]

Krstanovic et al.

[11] Patent Number: 5,453,170
[45] Date of Patent: Sep. 26, 1995

[54] OFF-COLUMN DETECTOR FOR ION SEPARATION TECHNIQUES

[75] Inventors: Srdjan Krstanovic, Windham, N.H.; James Reineck, Hull, Mass.

[73] Assignee: Ati Orion, Boston, Mass.

[21] Appl. No.: 312,463

[22] Filed: Sep. 26, 1994

[51] Int. Cl.⁶ .......................... B01D 61/42; C25D 13/00
[52] U.S. Cl. .......................................................... 204/299 R
[58] Field of Search ........................................ 204/299 R

[56] References Cited

U.S. PATENT DOCUMENTS

| | | | |
|---|---|---|---|
| 5,073,239 | 12/1991 | Hjerten | 204/299 R |
| 5,122,248 | 6/1992 | Karger et al. | 204/299 R |
| 5,244,560 | 9/1993 | Kuhr | 204/299 R |
| 5,358,612 | 10/1994 | Dasgupta et al. | 204/299 R |

Primary Examiner—John Niebling
Assistant Examiner—Bruce F. Beu

[57] ABSTRACT

An off-column conductivity detector for ion electrophoresis measurements is formed from a first connector having a body carrying the discharge end of a separation capillary and a second connector having a body carrying a measuring electrode. The geometry of the detector, and the relative positioning of the capillary and the measuring electrode within the connectors, result in an active measuring cell of precise and minute dimensions that provides measurements of high resolution and high sensitivity rapidly and reliably, despite the provision for rapid disassembly and reassembly by the end user for purposes of cleaning, electrode substitution, and the like.

22 Claims, 9 Drawing Sheets

|   | ppm |   | ppm |
|---|---|---|---|
| 1. BROMIDE | 4 | 13. TARTRATE | 5 |
| 2. CHLORIDE | 2 | 14. SELENITE | 10 |
| 3. FERROCYANIDE | 7 | 15. PHOSPHATE | 4 |
| 4. NITRITE | 4 | 16. CITRACONATE | 5 |
| 5. NITRATE | 4 | 17. GLUTARATE | 10 |
| 6. SULFATE | 4 | 18. PHTHALATE | 10 |
| 7. AZIDE | 2 | 19. CARBONATE | 4 |
| 8. OXALATE | 3 | 20. ACETATE | 10 |
| 9. MOLYBDATE | 5 | 21. CHLOROACETATE | 10 |
| 10. TUNGSTATE | 6 | 22. ETHANESULFONATE | 20 |
| 11. 1,2,4,5 BTC | 7 | 23. DICHLOROACETATE | 15 |
| 12. FLUORIDE | 1 | 24. PROPIONATE | 15 |
|   |   | 25. PROPANESULFONATE | 20 |
|   |   | 26. CROTONATE | 15 |
|   |   | 27. BUTANESULFONATE | 20 |
|   |   | 28. BUTYRATE | 15 |
|   |   | 29. TOLUENESULFONATE | 15 |
|   |   | 30. PENTANESULFONATE | 20 |
|   |   | 31. VALARATE | 15 |
|   |   | 32. HEXANESULFONATE | 20 |
|   |   | 33. CAPROATE | 15 |
|   |   | 34. HEPTANESULFONATE | 20 |
|   |   | 35. MES | 35 |
|   |   | 36. OCTANESULFONATE | 20 |
|   |   | 37. d-GLUCONATE | 40 |

FIG. 8B

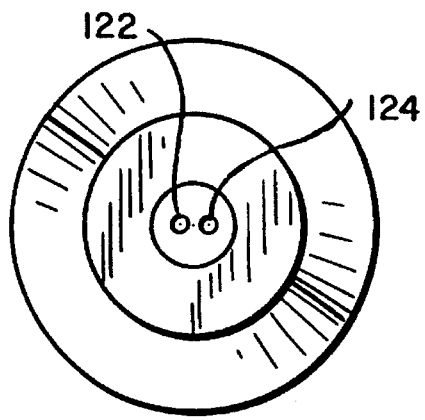
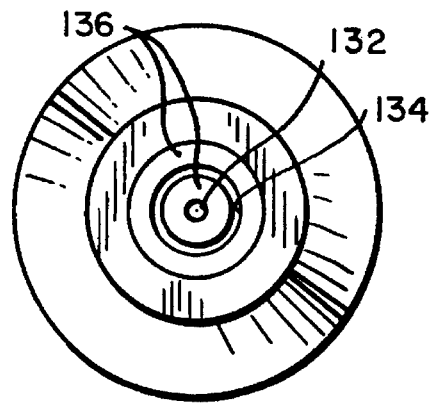
FIG. 11A  FIG. 12A
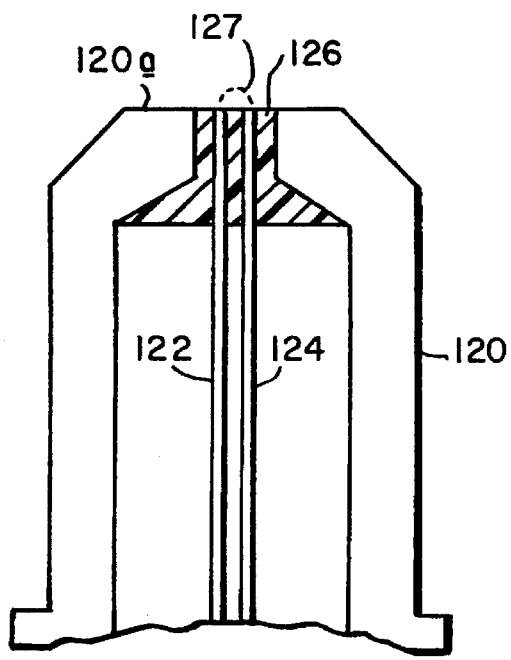
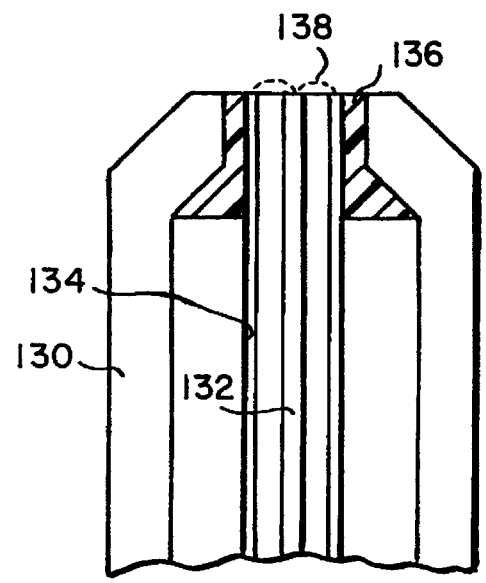
FIG. 11  FIG. 12

OFF-COLUMN DETECTOR FOR ION SEPARATION TECHNIQUES

BACKGROUND OF THE INVENTION

A. Field of the Invention

The invention relates to ionic separation techniques such as capillary ion electrophoresis and ion chromatography and, more particularly, to detectors for such techniques, especially conductivity detectors.

B. Prior Art

Capillary ion electrophoresis is a well known and highly useful technique for detecting and measuring ionic solutes. In this analytic technique, an analyte is flowed through a small bore capillary tube, along which an electric field is established. Typically, the field is on the order of 300 volts/meter. Ion constituents in the analyte move along the field at a rate dependent on their mobilities in the analyte solute. At the end of some period of time (e.g., several minutes in the case of a capillary tube on the order of a meter in length), the analyte zones at the discharge end of the capillary becomes highly concentrated with respect to the various ionic solutes within the analyte. This concentration changes as a function of time, characteristic of the different mobilities of the ions in the analyte solution.

A variety of means are used to detect the concentration of the solutes at or near the discharge end of the capillary. These include optical techniques such as fluorescence and ultraviolet absorption measurements; spectrometry; radioisotope tagging; and electrochemical and conductive measurements on the analyte, among others. The detectors may be placed "on-column" (that is, at a point near, but prior to, the discharge end of the capillary) or "off-column" (that is, post discharge).

Conductivity measurement is a form of detection that has been found to be especially simple for the user, reliable, accurate, and universal; thus it has become highly desirable for use in ion electrophoresis analysis. Both on-column and off-column conductivity detectors have been used. Off column detectors are less susceptible to the interference that commonly arises from the high voltage along the column required for ion separation, and have a lower cell constant and thus higher sensitivity. However, they frequently suffer from diminished resolution. A brief review of such detectors, and an analysis of one form of off-column detector, is given in Huang and Zare, *End Column Detection For Capillary Zone Electrophoresis*, Anal Chem. 1991, 63, 189–192.

SUMMARY OF THE INVENTION

A. Objects of the Invention

Accordingly, it is an object of the invention to provide an improved off-column detector for ion electrophoresis analysis.

Further, it is an object of the invention to provide an improved conductivity detector for ion electrophoresis analysis that is characterized by enhanced sensitivity and resolution.

Still a further object of the invention is to provide an improved off-column conductivity detector for ion electrophoresis analysis that is cost effective, simple and reliable to use, and that provides improved sensitivity and resolution.

B. Brief Description of the Invention

In the preferred embodiment of the present invention, an off-column conductivity detector for capillary ion electrophoresis analysis is formed from first and second connectors which precisely and repeatably position a measuring electrode and the discharge end of a separation capillary opposite each other with tightly controlled spacing and relative location. The separation capillary, and the active electrode end of the detector, are held within connectors of the type commonly used for optical fiber connections. Such connectors have a body for holding the fiber and a threaded head secured to the body but freely rotatable about it for securing the connector to an object via the threaded head. These connectors are described in more detail in the copending application of Srdjan Krstanovic, "Connectorized Capillaries For Use With Separation Instrument Components", Ser. No. 08/031,007, filed Mar. 12, 1993 and copending herewith; the contents of that application are incorporated herein by reference.

In the preferred embodiment described herein, the end face of the separation capillary connector body is crossmilled to provide intersecting channels or grooves for liquid flow across the face. The separation capillary is positioned at the intersection of the channels and is offset inwardly from the plane of the end face of the connector. A second connector, of a type similar to the first but without the cross-milling in the end face, carries an insulated detector electrode extending axially through the detector body and terminating in the plane of the end face. The electrode is surrounded by insulating material forming an annular ring around it. An alternating or pulsed electric field is applied across this ring by applying a voltage between the electrode and its connector body.

A detector cell has a main bore extending therethrough between opposite faces thereof to receive the connectors in opposed relation. Additional fluid bores connect with this bore at a defined location to provide a path to a ground reservoir and to supply flushing fluid to the bore and remove fluid therefrom. When the connectors are inserted into the main bore, the end faces of the connectors butt against each other and thereby precisely fix the location of the end face of the capillary in the first connector with respect to the measuring electrode in the second connector.

This defines a measuring volume of minute and controlled dimensions which is thereby characterized by a measuring cell constant of small magnitude and thus substantial sensitivity and resolution. This enables accurate and repeatable measurements of ion concentrations in the analyte discharged from the capillary, even at concentration levels of part per billion (ppb) and, in some cases, of parts per trillion (ppt).

BRIEF DESCRIPTION OF THE DRAWINGS

The foregoing and other and further objects and features of the invention will be more readily understood on reference to the following detailed description of the invention when taken in connection with the accompanying drawings in which:

FIGS. 11 and 12 a diagrammatic side sectional views of alternative arrangements of sensor electrodes in accordance with the present invention, and FIGS. 11A and 12A are end vies of the sensor connectors of FIGS. 11 and 12.

DETAILED DESCRIPTION OF THE INVENTION

Figure 1:
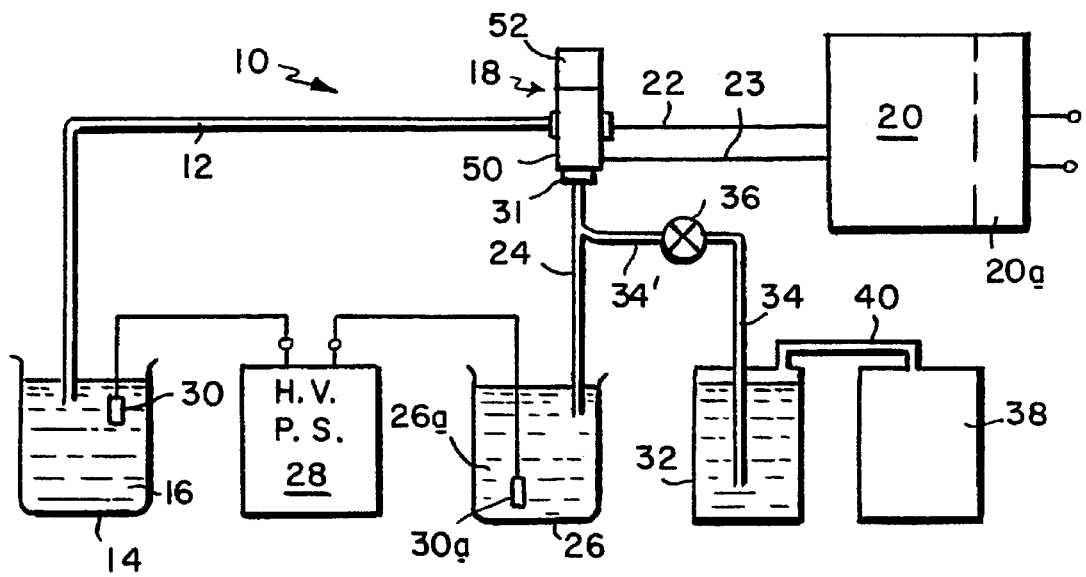
FIG. 1 is a schematic diagram of a capillary ion electrophoresis measuring system incorporating the conductivity detector of the present invention.

Turning now to FIG. 1, a capillary ion electrophoresis instrument 10 in accordance with the present invention has an electrically insulated capillary 12 extending into a container 14 holding a liquid 16 to be examined. The liquid typically is an eluent formed by diluting the material of interest in water, for example, but may in fact be any analyte of interest. The capillary carries the eluent to a detector 18 which is connected to measuring electronics 20 via lead wires 22. Additional lead wires 23 connect heater controller elements in the detector to the electronics 20. Fluid drains from the detector via a nonconductive line 24 into a discharge container 26.

A high voltage power supply 28 applies a voltage along the capillary via electrode 30, immersed in eluent 16, and electrode 30a, immersed in the waste liquid 26a of container 26. Power supply 28 is of sufficient voltage to apply a gradient along the capillary on the order of up to approximately 300 v/m (volts per meter) as is common in capillary ion electrophoresis measurements. For a one meter length of capillary 12, as is common in capillary ion electrophoresis, power supply 28 is on the order of 30,000 volts.

Figure 2:
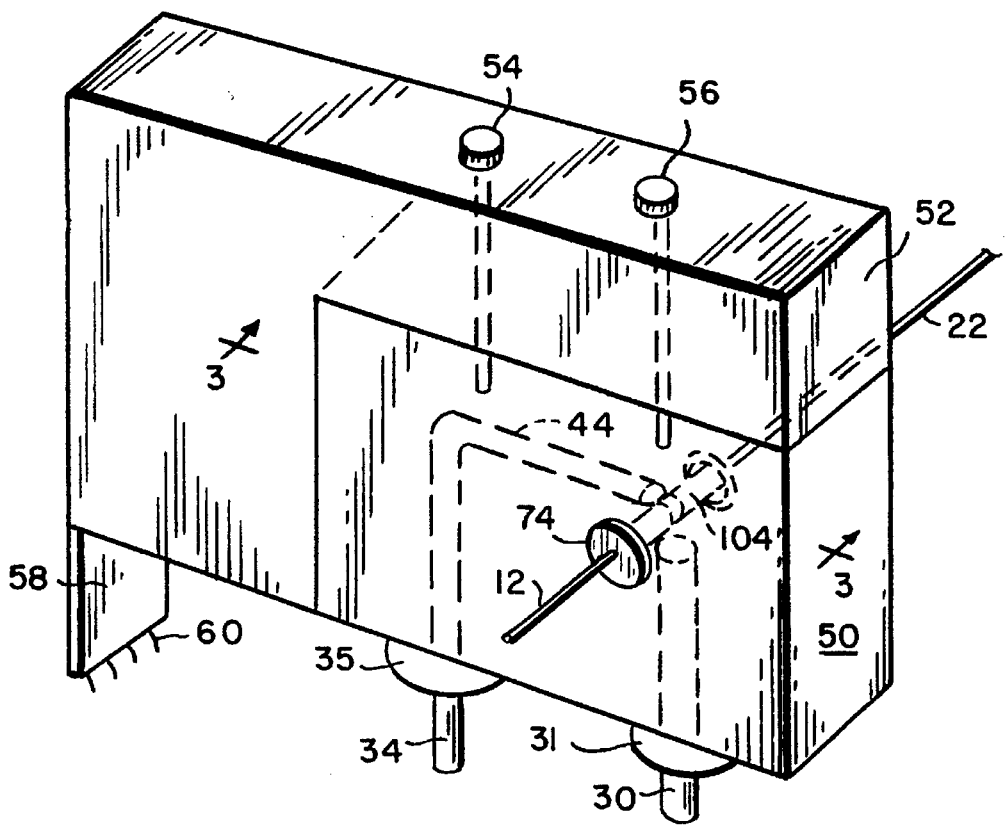
FIG. 2 is a stylized view in perspective showing the detector of the present invention.
Figure 3:
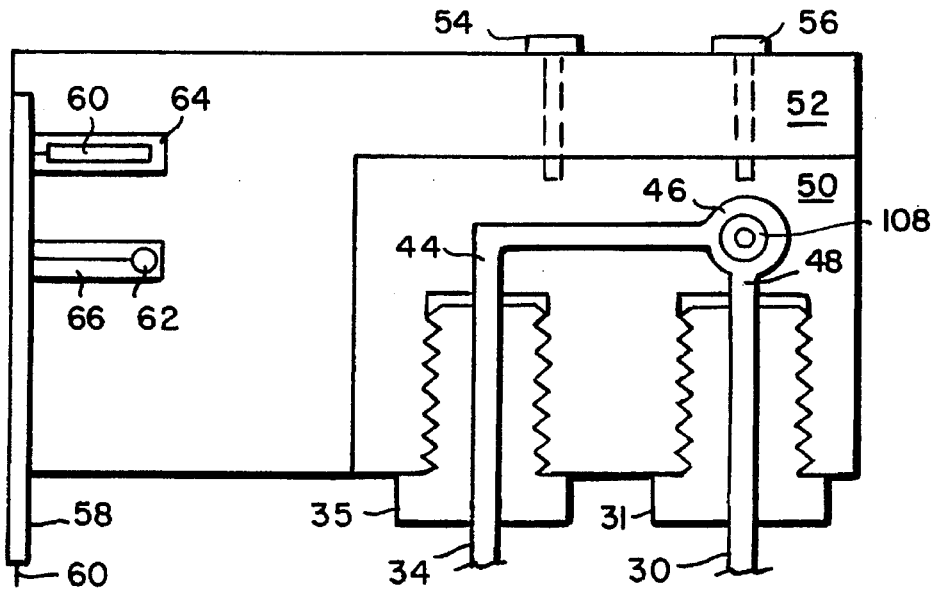
FIG. 3 is a side view of the detector of FIG. 2.

A source 32 of flushing solution is connected to the detector 18 via a fluid line 34, 34' and connector 35 (FIGS. 2, 3). A valve 36 interposed in the line 34, 34' is controlled from measuring and control electronics 20 and is opened after measurements are performed to thereby flush the detector with liquid from source 32. The flushing liquid is also discharged from cell 50 via line 24 and thence into waste receptacle 26. The flushing solution is pressurized from a source 38 via a pressure line 40 and corresponding connectors. Typically, the source 38 comprises a pressurized container of air or of an inert gas such as nitrogen, or may alternatively comprise an air pump or the like.

The measuring and control electronics are preferably decoupled from the return path of the power supply 28 in order to eliminate noise pickup. A level translator 20a in the electronics references the output signal to a common ground level for interface to subsequent data collection, processing and display systems.

The high voltage used to drive the capillary also causes electrolysis byproducts to form in the waste eluent during the analysis. These byproducts, as well as dissolved gasses frown the atmosphere, can modify the background conductivity of the eluent and thus cause baseline drifts and noise. To eliminate this source of error, the tubing 24 is formed of a much larger diameter than the capillary 12 (e.g., thirty three times as large), so that the electric field in the tubing 24 is of the order of one thousandth that within the capillary 12. In consequence, impurities from the waste receptacle 28 migrate back toward the detector 50 at a markedly slower rate than the migration rate of the eluent through the capillary 12.

FIGS. 2 and 3 show the detector 18 in more detail. In accordance with the preferred embodiment of the invention, the detector comprises an active fluidics cell segment 50 and a passive thermal mass 52 in thermal engagement with the segment 50. The thermal mass helps to regulate the temperature of the measuring cell and maintain it relatively constant over a given measurement interval. Screws 54, 56 tightly clamp the two sections together. A printed circuit board 58 mounted on an end of the thermal mass 52 carries a heater 60 and a thermistor 62; these elements fit into bores 64, 66, respectively, formed in the mass 52 and maintain the mass 52, and thus the fluidics cell 50, at a constant temperature. Leads 60 connect the board 58 to the measuring and control electronics 20 (FIG. 1) which monitors the temperature as measured by the thermistor 62 and actuates the heater element 60 as necessary to maintain a desired constant temperature during measurements. An internal bore 44 connects the flushing supply line 34 via a connector 35 to a bore 46 extending through the opposed faces of cell 50 from one face thereof to the other. The capillary detector 70 (FIG. 4) and sensor electrode detector 100 (FIG. 5) meet in this cavity, where the eluent discharged from the capillary is analyzed by the sensor. Liquid is discharged from this cavity to the waste receptacle 28 (FIG. 1) by way of a discharge bore 48 that is connected to the discharge line 30 via connector 31.

As may be seen more clearly frown FIG. 3, the length of the discharge bore 48 that extends within the cell body 50 between the detector cavity and the discharge line 30 is extremely short (e.g., on the order of 0.5 millimeters). Thus, even though the cell body may be formed of electrically conductive material, the potential drop across the fluid segment in the bore 48 is small, and less than the potential at which electrolysis occurs., This eliminates bubble formation and consequent ion contamination in the cell which would otherwise lead to baseline noise and drift. The result is a highly stable cell.

Figure 4:
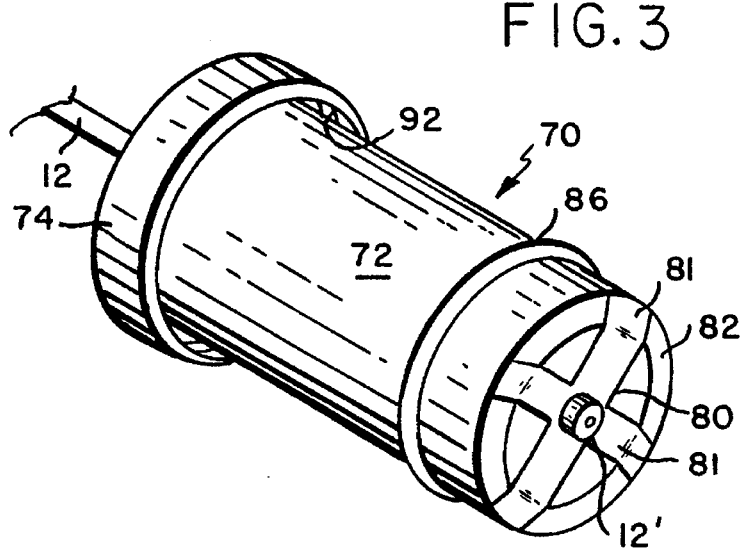
FIGS. 4 and 5 are stylized views in perspective of the capillary and detector heads, respectively, of the detector of the present invention.
Figure 5:
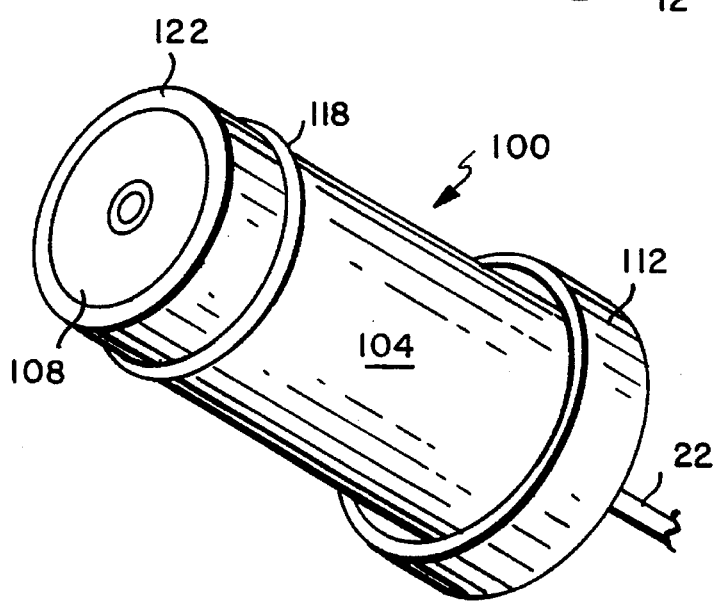
Figure 6:
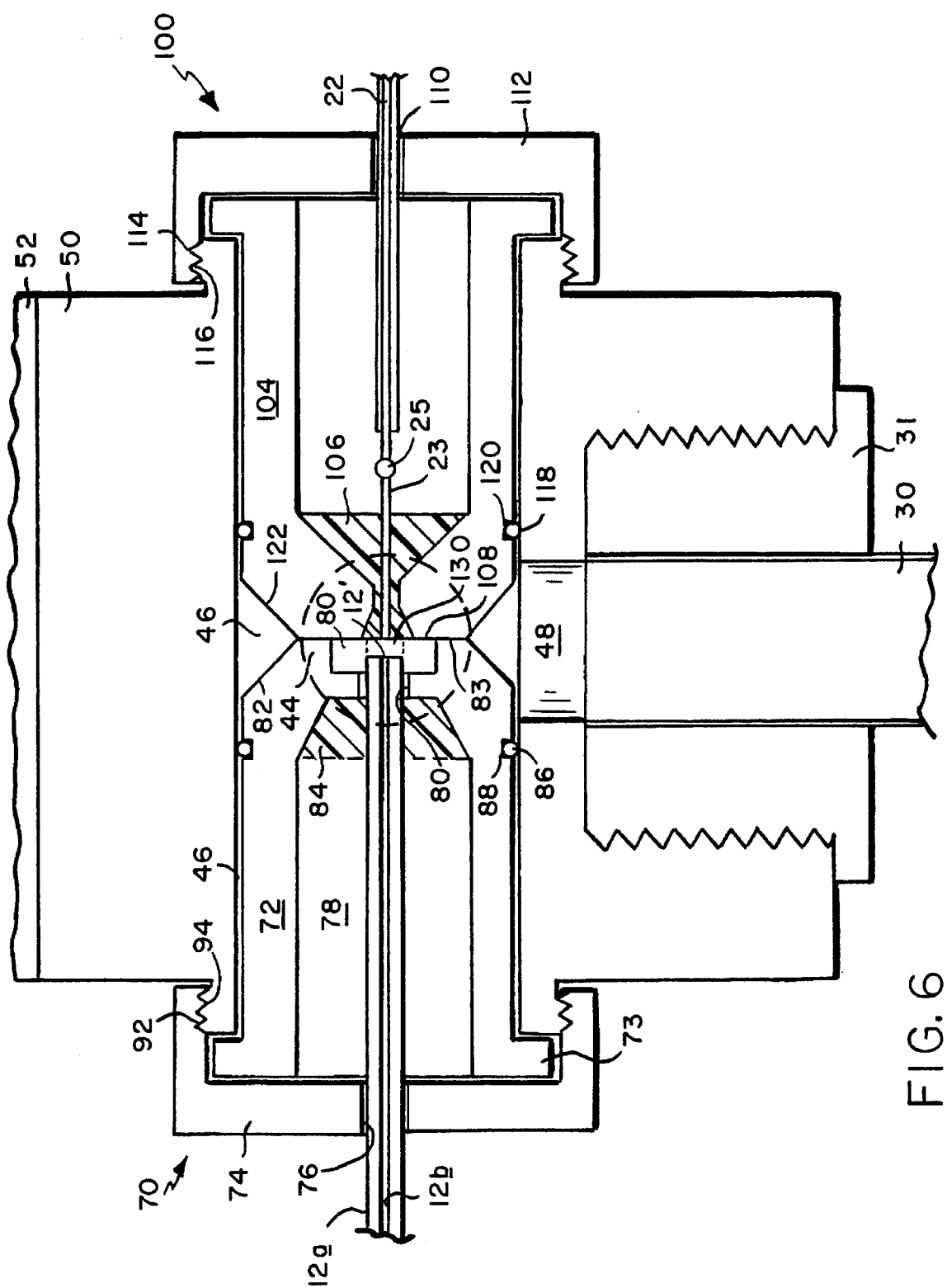
FIG. 6 is a side sectional view of the detector of the present invention along the lines 6—6 of FIG. 2.

With reference now to FIGS. 4-6, as well as FIGS. 1-3, capillary 12 comprises hollow cylindrical tubing having an outer wall 12a and an inner central bore 12b which carries the eluent. The wall 12a is non-conductive. Capillary 12 is secured within a capillary detector 70 having a connector body 72 and an internally threaded cap 74 anchored longitudinally along the body but freely rotatable about the longitudinal axis of the body. One such connector that we have employed usefully in the invention is a fiber optic connector manufactured by the Amphenol Corporation and identified as their 905-150-5002 connector. In the present invention, the capillary 12 is extended through a bore 76 in the cap, through an interior cavity 78 in the connector body 72, and through a cavity 80 extending through an inwardly sloping shoulder 82 formed at the front face 83 of the connector body 72. The cavity 80 is formed from rectilinear slots 81, milled transversely across the shoulder (FIG. 4). Epoxy 84 anchors and seals the capillary 12 in the connector 70.

Figure 7:
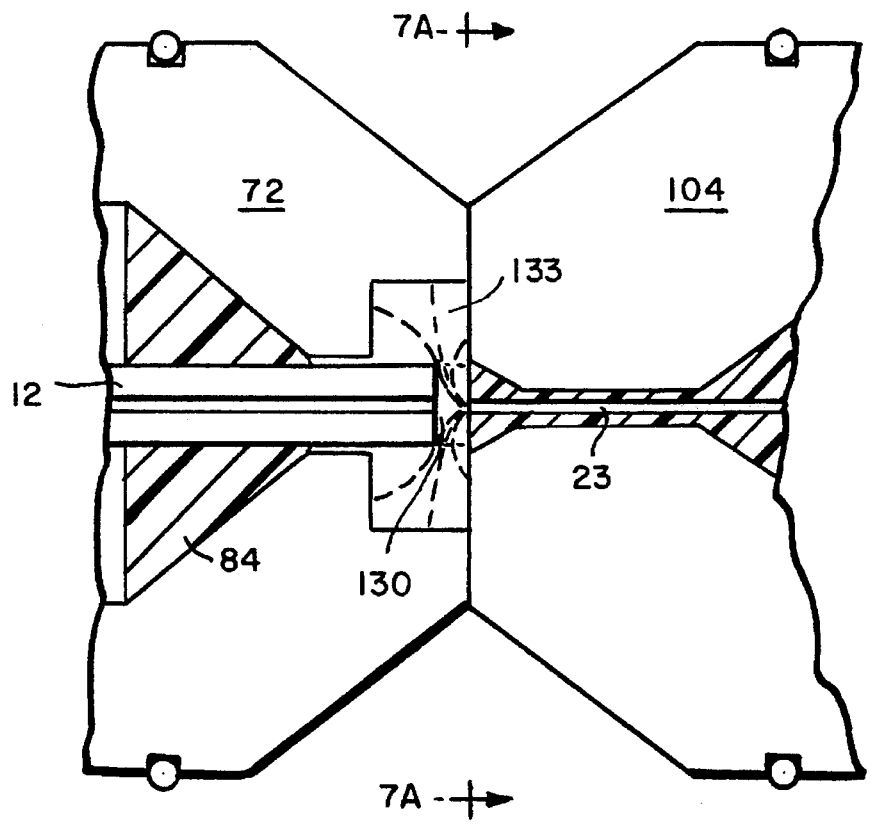
FIG. 7 is an enlarged view of a portion of FIG. 6 showing the abutting capillary and detector heads in more detail.
Figure 7A:
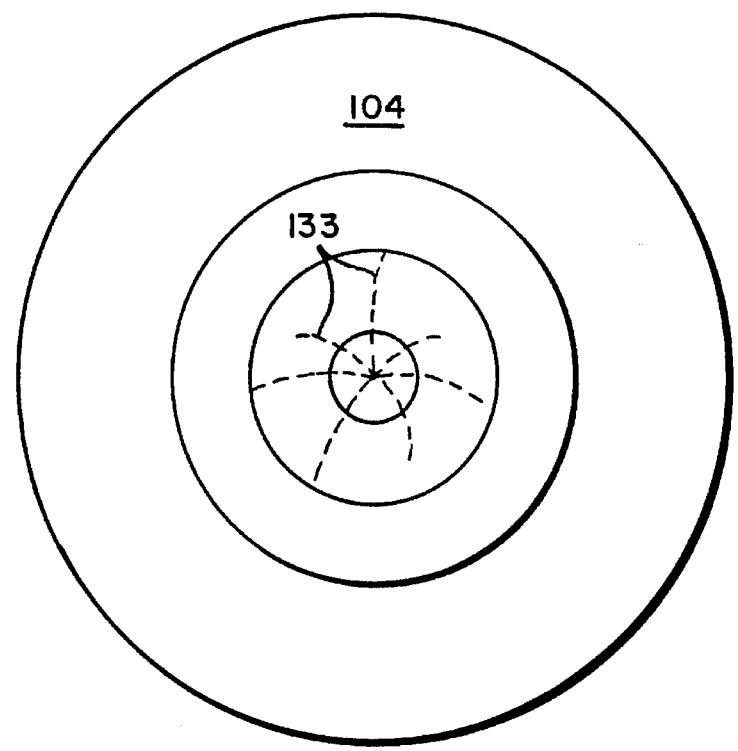
FIG. 7A is a cross section along the line 7A—7A of FIG. 7.

As may be seen from FIGS. 4 and 6, and as will be described more fully below, the end face 12' of capillary 12 terminates a short distance behind the facial plane of the end face 83 of connector 70. An O-ring 86 is received within an annular groove 88 formed on the periphery of body 72. Body 72 fits snugly within bore 46. The O-ring 86 prevents fluid discharged frown the capillary 12 from flowing backwardly along the bore 46. A cap 74 on connector 70 secures the capillary to the cell 50. To this end, the cap has an interior thread 92 which mates with a corresponding thread 94 formed on the cell 50; when the threads engage each other, cap 74 pushes against a shoulder 73 on connector 70 to snugly seat the connector Facing connector 70 within bore 46 is a second connector 100 which carries insulated lead wire 22 from the cell 50 to the measuring and control electronics 20 (see also FIG. 1). Lead wire 22 is connected to an active sensing electrode 23 via 25 or the like. The sensing electrode 23 preferably comprises an insulated wire of platinum, gold, or the like, and extends from the front face 108 of body 104 through a bore 110 in a cap 112 of connector 100. In the preferred embodiment of the invention now being described, wire 23 comprises one electrode of the conductivity sensor; it is fixed within a centrally-formed bore within body 104 of connector 100 by means of epoxy 106. As may be seen more clearly in FIG. 7, the epoxy may flare outwardly at the end face 108 of connector 100 to thereby define an annular ring surrounding the electrode 23 at the end face. The body 104 is electrically conductive and comprises the second electrode of the conductivity sensor. An alternating electric field is established between the conductor electrode 23 and body 104 by the measuring and control electronics 20. Eluent discharged from the capillary 12 traverses this field and the resultant current between the electrodes 23, 104 is a direct indication of the conductivity of the eluent.

As was the case with cap 74 of connector 70, cap 112 of connector 100 is anchored longitudinally along the body 104 of connector 100 but is freely rotatable about the longitudinal axis of the body. It has an interior threaded surface 114 which mates with a corresponding threaded boss 116 of cell 50. An O-ring 118 in an annular groove 120 seals the bore 46 against flow of fluid along the body 104 toward the cap 112.

Body 104 has a shoulder 122 tapering away from the front face 108 and forming, with the tapered shoulder 82 of connector 70, a V-shaped annular channel 46 extending around the periphery of the end faces of the connector bodies 72, 104 and in liquid communication with flushing and discharge channels 44 (shown in dotted lines in FIG. 6) and 48, respectively. In particular, eluent exiting from the capillary 12 passes across the face 108 of connector 100, into the V-shaped annular bore 46, and thence is discharged into the waste receptacle 26 through the bore 48. Similarly, flushing liquid supplied to cavity 46 via liquid line 34 and bore 44 passes both around the periphery of the end faces of connectors 70 and 100, as well as through the slots 81, 83 in the face of connector 70, thereby sweeping across the discharge end of the capillary 12, as well across as the face of the connector 100. These liquids drain through the discharge port 48 and thence through to waste receptacle 28.

The gap between the end face of capillary 12 and the sensor wire 23 defines a generally cylindrical measuring cell 130. This cell is extremely small in extent and volume, and thus has a low cell constant and a resultant high sensitivity. As shown more clearly in FIG. 7, a measuring signal applied by the electronics 20 between the wire 23 and the body 104 creates an electric field 133 extending generally transversely within the cell between the wire 23 and the connector body 104, parallel to the end face of the body 104. The field terminates primarily on the body 104, although some of it extends to the body 72. By virtue of the geometry of the connectors and the surrounding housing, and the positioning of the capillary discharge relative to the measuring electrode, the field established by the electrode has substantial intensity throughout the entire region of the active measuring volume or cell 130, and thus the conductivity of eluent discharged into this volume is measured with high sensitivity. In particular, the end face of wire 23 is positioned to be physically more remote from the connector body 72 or from other conductive regions of the housing to which the electric field might otherwise bridge than it is from the discharge end of the capillary 12, thus ensuring that, for a given potential applied to the wire 23, a higher proportion of the resultant field intercepts the eluent than would otherwise be the case.

The construction described herein provides precise and repeatable positioning of the capillary discharge in relation to the active measuring electrode. When assembled within the main or measuring bore of the detector cell, the end faces of the connectors butt against each other, thus defining the capillary-to-active electrode spacing and their radial positioning. Because of this, the spacing is inherently repeatable, despite disassembly of detector by the user for purposes of cleaning, or in order to change the detector or capillary, or for other reasons. The construction readily accommodates other types of sensors, such as amperometric, optical, solid state, ISE, and the like, which can readily fit within the geometry of the connector 100.

As an example of the construction of a particular embodiment of the present invention and the results achieved with it, a capillary 12 of 360 micron outer diameter and 50 micron inner diameter was assembled in a fiber optic connector body 72 of ⅛ inch outer diameter. The capillary terminated sufficiently short of the end face of the connector body to define a gap of approximately 25 microns between the capillary end face and the sensing or measuring conductor 23. The measuring conductor 23 had a diameter of approximately 150 microns and an insulating cladding of approximately 10 to 15 microns. An annular insulating span surrounding the measuring electrode 22 at the end face thereof of approximately 350 microns in width was established by the insulating coating 106. This resulted in a conductivity detector with an effective cell volume of approximately three nanoliters and a sensitivity sufficient to detect cation and anion concentrations as low as ten parts per trillion. To give an example of this level of sensitivity, it is equivalent to detecting a change in the current U.S. national debt of as little as $40!

Figure 8A:
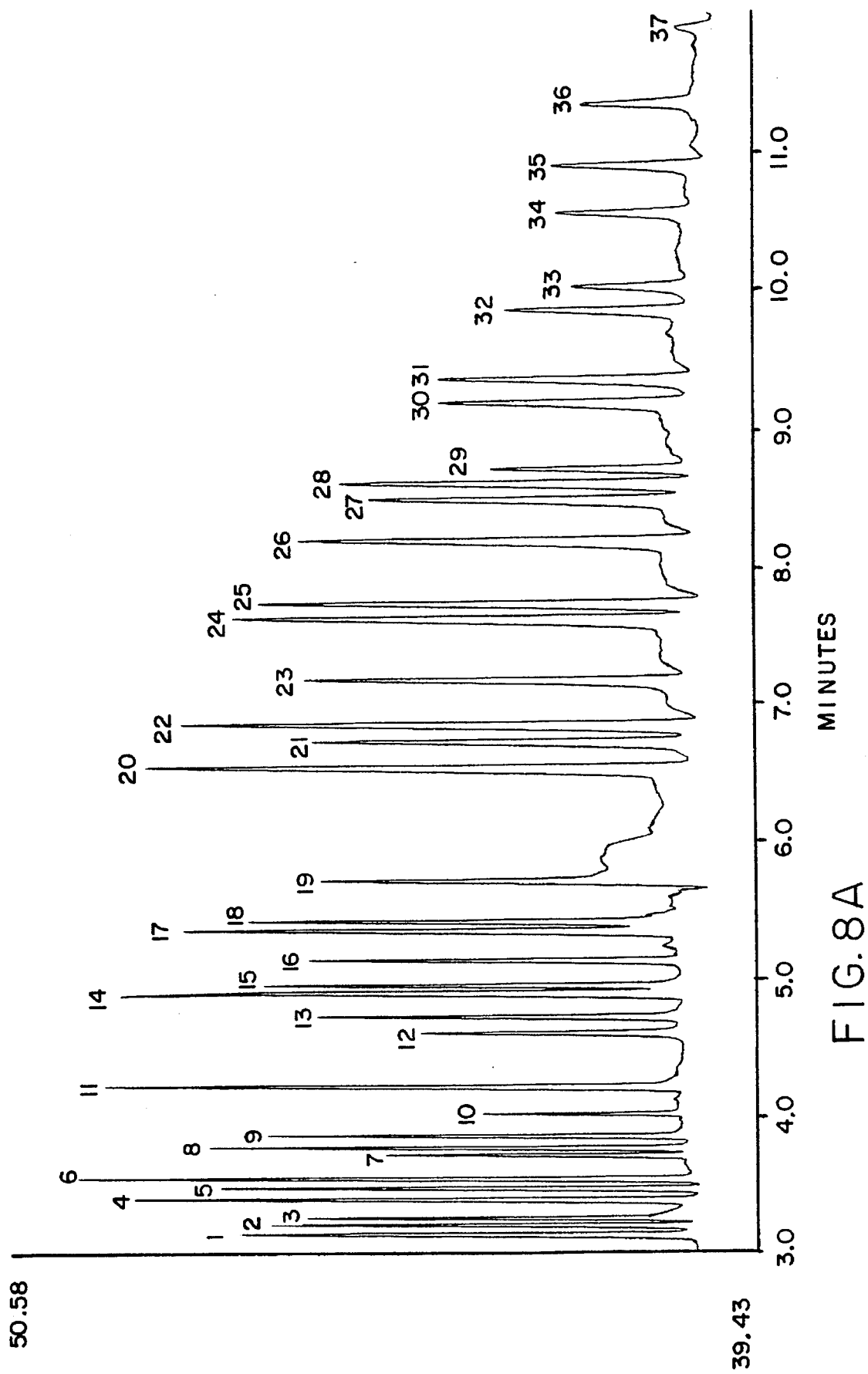
FIGS. 8 and 9 are charts of sample measurements made with the conductivity detector of the present invention.

FIG. 8 is a graph of an illustrative measurement made with the detector of the present system. The vertical axis shows the measured relative conductivity of various ions, while the horizontal axis shows the time in minutes after injection of the sample. The numbered peaks designate the corresponding detected ions listed in FIG. 8, and their concentrations in parts per million (ppm).

Figure 9:
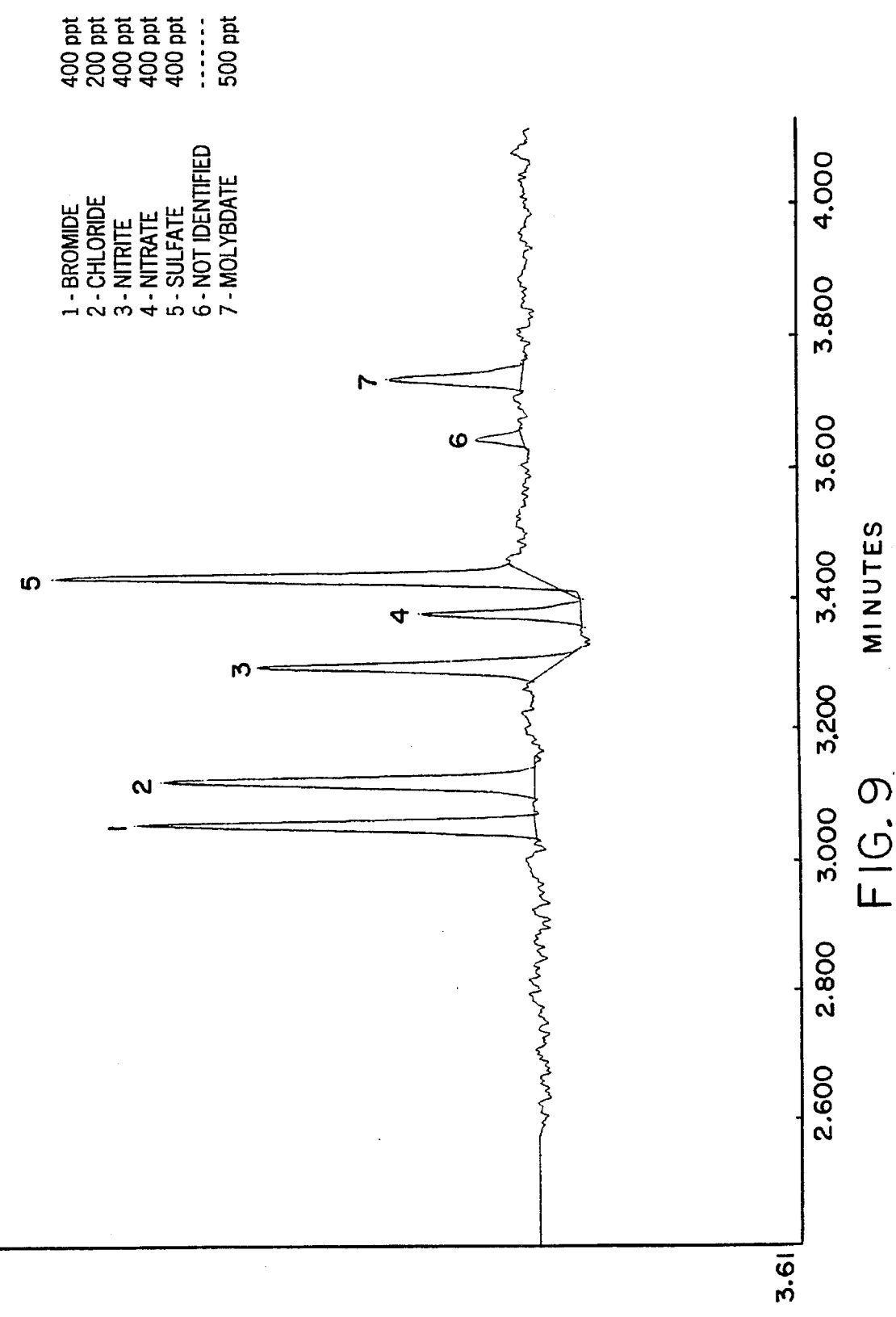

FIG. 9 shows an even further example of the sensitivity of the detector of the present invention. Concentrations on the order of several hundred parts per trillion were readily detected for the ions listed therein with a signal to noise ratio, S/N, of approximately twenty.

It can be seen from FIGS. 8 and 9 that the detector of the present invention is sensitive; stable (i.e., relatively little drift); low in noise; and has good resolution. This is largely a consequence of the close and precise positioning of the discharge capillary end face in relation to the measuring electrode as provided by the present invention.

In the preferred embodiment of the invention described so far, the desired spacing between the discharge end of the eluent-supplying capillary and the measuring electrode is maintained by terminating the capillary end face short of the end face of the connector in which it is mounted; the end face of the measuring electrode is flush with the connector in which it is mounted. The opposite configuration can, of course, be utilized, that is, the end face of the capillary mounted flush with the end face of its connector and the end face of the measuring electrode inset by a predetermined amount behind the end face of its connector, the flushing cross channels being then formed in the electrode connector in the manner described in the preferred embodiment for the capillary connector.

In both configurations described above, the spacing is maintained by butting the end faces of the connectors together within the housing to thereby precisely define the measuring cell. This has been proven to be a rapid, reliable and repeatable approach for even very low level ion measurements. An alternative approach is to establish the dimensions of the measuring cell by providing a spacer within the main measuring bore against which the respective capillary and measuring connectors butt. The spacer may be formed integral with the detector housing by milling the detector block from opposite faces, leaving a slight annular ridge of defined thickness within the cavity against which the respective connectors butt and which thus defines the thickness of the measuring cell. In this case, the end faces of both the capillary and the measuring electrode are flush with the face of their respective connectors. Alternatively, the spacer can be a separate washer inserted into the bore. In either case, however, because of the minute thickness of the spacer, it is more susceptible to inadvertent damage by the user.

Further, although the measuring electrode has been described in the form of a single central electrode which uses the connector body as its second electrode, the electrode sensor may alternatively comprise an insulated central wire lead coaxially surrounded by a cylindrical tubular lead, both electrodes being mounted axially in the electrode connector and operating essentially as described in connection with the preferred embodiment described in detail herein. Alternatively, the measuring electrode may be formed from a pair of wires axially mounted in the electrode connector. Either of these configurations allow the use of a non-conductive body for the electrode connector, but typically have lesser sensitivity than the preferred embodiment described herein.

Figure 10:
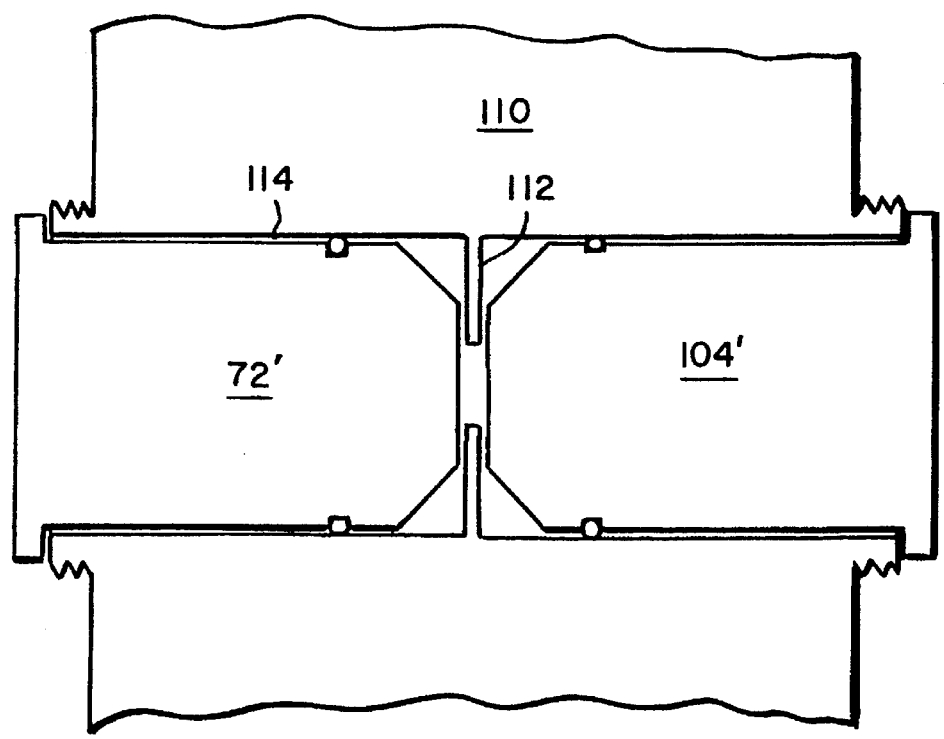
FIG. 10 is a diagrammatic view of an alternative form of spacer for defining the measuring cell.

These alternatives are described in more detail in connection with FIGS. 10–14. In FIG. 10, cell housing 110 is essentially identical to cell housing 50 of FIGS. 1–7 but has an annular flange 112 formed in its bore 114. Flange 112 separates capillary body 72' and sensor body 104' by a precise amount which determines the cell constant. Bodies 72' and 104' are essentially identical to the respective bodies 72 and 104 of FIGS. 3–7, but the capillary 12 now terminates at the face of the body 72', instead of inwardly thereof as was the case with capillary body 72.

The construction of FIG. 10 simplifies the task of manufacturing the capillary connector of FIGS. 4–7, since the capillary exit orifice need not be offset inwardly of the end face of the connector body. However, this is accomplished at the expense of increased difficulty in manufacturing the cell housing, since great care is required to form the annular ring 112 to the requisite tolerance. Further, since this ring is extremely thin (on the order of 25 microns), it is susceptible to damage from excessive tightening when assembling the cell and connectors.

The flange 112 may alternatively be replaced with an annular ring or washer inserted separately in the bore of the cell housing when inserting the capillary and sensor bodies, or may be formed on or attached to one of the bodies prior to insertion. Again, this offers advantages in construction of the capillary or sensor bodies, but is susceptible to damage in handling by the user.

FIGS. 11 and 12 illustrate alternative forms of conductive sensors for use in the present invention. In FIG. 11, the sensor body 120 carries first and second side-by-side insulated lead wires 122, 124 extending in an axial direction through the body and terminating in a flat face 120a of the connector body. The wires are embedded in epoxy 126 to fix their position. An electric field 127 established between the wires by the measuring and control electronics 20 as illustrated illustratively at 126 provides the means for establishing a current between the wires when the body 120 is positioned opposite the discharge of an eluent source such as the capillary 12 of FIG. 6. This configuration allows the body 120 to be made of insulating material.

In FIG. 12, a detector body 130 has a central conductor 132 coaxially disposed within an outer cylindrical conductor 134. The conductors are fixed in epoxy 136 which fixes their spacing and their location within the body 130. An alternating potential applied between the conductors 132, 134 by the measuring and control electronics 20 establishes a field 138 between them which allows measurement of the current established by eluent flow across the field when the body 130 is positioned opposite an eluent source as in FIG. 6. As was the case with the sensor of FIG. 11, the construction of the sensor of FIG. 12 allows use of a non-conductive body 130.

Figure 13:
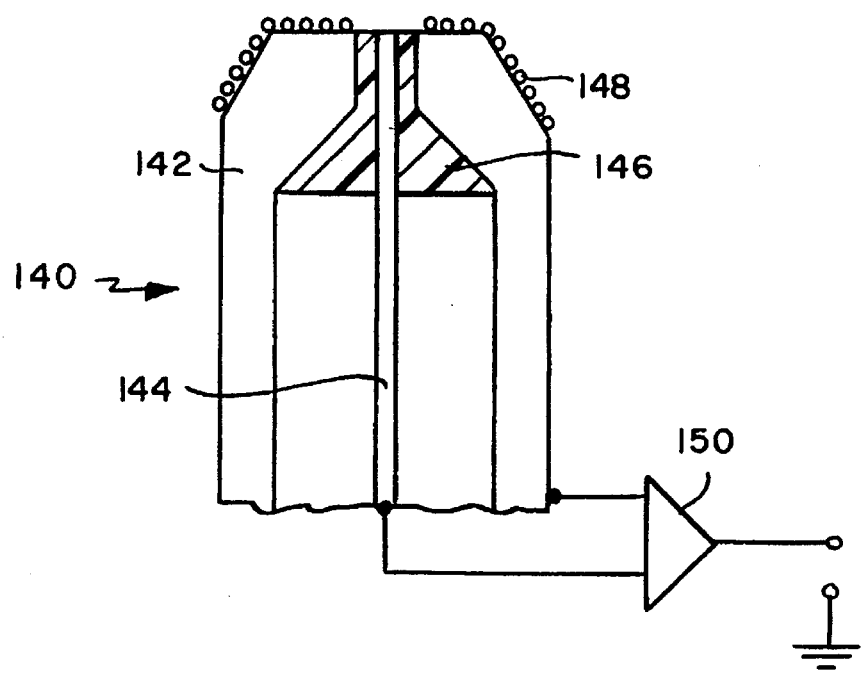
FIG. 13 is a diagrammatic side sectional view of an electrochemical sensor that may be used with the measuring cell to form an amperometric or potentiometric detector in accordance with the present invention instead of a conductivity detector.

Finally, FIG. 13 shows yet another form of electrode that may advantageously be used in the present invention, namely, an electrochemical sensor e.g., a Ag-AgCl electrode. A sensor connector 140, similar in physical geometry to the connector 100 of FIGS. 4–7, has a cylindrical body 142 in which is carried a central working electrode 144 of Ag or the like imbedded in the epoxy of 146. The body 142 is of conductive material, e.g., silver or the like, and is coated at its forward end with AgCl 148 to form an amperometric detector. The conductor 144 and body 142 are shown as illustratively connected to a suitable measuring instrument 150 which measures the amperometric current flowing as a result of oxidation-reduction reactions at the sensor electrodes when the sensor is exposed to eluent from capillary 12 as in FIG. 6.

As noted previously, the detector geometry of the present invention provides a measuring cell of precise and repeatable dimensions and location, thus providing a sensitive, reliable detector with good resolution and substantial ease of use even by personnel of limited training. The cell volume is preferably defined by using a sensor connector having its end face flat and mated with a capillary connector whose discharge orifice is inwardly offset from the end face of the connector body in which it is mounted. It will be understood, of course, that the sensor elements may, conversely, be inset, and the capillary connector terminated flush with the end face of the connector body in which it is mounted. Further, the various spacing arrangements discussed above in connection with FIG. 10, among others, may also be used.

What is claimed is:

1. A detector for ion-responsive measurements, comprising:

A. a capillary mounted in a first body and having an exit orifice for discharging eluent therethrough;

B. a sensor mounted in a second body for measuring a characteristic of eluent passing said sensor;

C. a cell housing having a main bore extending through a pair of opposed faces for removably receiving said bodies therein: and positioning them in face-to-face alignment with said capillary exit orifice opposite said sensor and separated therefrom to thereby define a measuring cell between said capillary exit orifice and said sensor.

2. An ion-responsive detector according to claim 1 in which said bodies have end faces which butt against each other when positioned in said bore for measurement, and in which at least one of said capillary exit orifice and said sensor are located inwardly of its respective end face.

3. An ion-responsive detector according to claim 2 in which said first body comprises a cylindrical rod having a bore extending axially therethrough and mounting said capillary therein.

4. An ion-responsive detector according to claim 3 which includes means forming a fluid channel in said end face and extending transversely from said capillary exit orifice, and in which said exit orifice terminates within said fluid channel and inwardly of said end face.

5. An ion-responsive detector according to claim 4 in which said second body comprises a cylindrical rod having a bore extending axially therethrough and mounting a sensor therein having an active element at an end face thereof facing said capillary exit orifice.

6. An ion-responsive detector according to claim 5 in which said sensor comprises first and second electrodes establishing an electric field between them, said field projecting into said measuring cell and having a substantial component transverse to the axial direction.

7. An ion-responsive detector according to claim 6 in which said electrodes are coaxially mounted in said second body.

8. An ion-responsive detector according to claim 7 in which said second body forms one of the sensor electrodes.

9. An ion-responsive detector according to claim 2 in which said second body comprises a cylindrical rod having a bore extending axially therethrough and mounting a sensor therein having an active element formed inwardly of an end face thereof facing said capillary exit orifice.

10. An ion-responsive detector according to claim 9 in which said sensor comprises first and second electrodes establishing an electric field between them, said field projecting into said measuring cell and having a substantial component transverse to the axial direction.

11. An ion-responsive detector according to claim 1 in which said sensor comprises an electrochemical sensor.

12. An ion-responsive detector according to claim 11 in which said sensor comprises a Ag-AgCl sensor having a Ag lead wire mounted in said second body and terminating in a face of said body opposite said exit orifice, and a AgCl coating formed on said face and surrounding said lead wire.

13. An ion-responsive detector according to claim 1 in which said cell housing further includes a discharge channel connecting with said main bore and of a length short enough to preclude electrolysis of eluent therein along the length thereof.

14. An ion-responsive detector according to claim 1 which includes means within said cell housing for spacing said capillary and said sensor.

15. An ion-responsive detector according to claim 14 in which said means comprises an annular ring formed within said bore.

16. An ion-responsive detector according to claim 1 which includes a spacer element for insertion into said bore between said capillary and said sensor to thereby establish the spacing between them.

17. An ion-responsive detector according to claim 1 which further includes a mass of high thermal conductivity in thermal contact with said cell, said mass including means for sensing the temperature thereof and means for heating said mass in response to the sensed temperature therof.

18. A sensor for ion-responsive measurements, comprising:

A. means forming a body for fluid-tight insertion into a detector cell housing and for repeated engagement and disengagement with said housing;

B. means forming a sensor on an end face of said body for interaction with eluent supplied to said sensor when mounted in said cell housing.

19. An ion-responsive detector according to claim 18 in which said body comprises a cylindrical rod having a bore extending axially therethrough for mounting at least a first electrode therein, said rod snugly fitting within a corresponding bore in said cell housing with said electrode positioned such that eluent washes over the face thereof when the rod is mounted within said bore.

20. An ion-responsive detector according to claim 19 which includes a second electrode on said body.

21. An ion-responsive detector according to claim 20 in which said second electrode is mounted coaxial with said first electrode for measuring the conductivity of eleuent passing across said electrodes.

22. A detector for ion-responsive measurements, comprising:

A. a capillary mounted axially in a cylinder;

B. a sensor mounted axially in a cylinder;

C. a cell having a bore sized to snugly receive the cylinders in opposed relation and butted against each other to thereby define a measuring cell of restricted dimensions between the discharge end of the capillary and the active face of the sensor.

* * * * *